(12) United States Patent
Kato et al.

(10) Patent No.: US 6,248,534 B1
(45) Date of Patent: Jun. 19, 2001

(54) METHOD FOR DETERMINING THE DETECTION VALUE OF A TARGET RNA

(75) Inventors: Kikuya Kato, 4-1-8, Nagaremachi, Hirano-ku, Osaka-shi, Osaka-fu; Ryou Matoba, Sakai, both of (JP)

(73) Assignees: Kikuya Kato; Unitech Co., Ltd., both of (JP)

( * ) Notice: Subject to any disclaimer, the term of this patent is extended or adjusted under 35 U.S.C. 154(b) by 0 days.

(21) Appl. No.: 09/448,478

(22) Filed: Nov. 24, 1999

(30) Foreign Application Priority Data

May 25, 1999 (JP) ................................. 11-145440

(51) Int. Cl.[7] .............................. C12Q 1/68; C12P 19/34; C07H 21/02; C07H 21/04
(52) U.S. Cl. ......................... 435/6; 435/91.1; 435/91.2; 435/91.21; 536/23.1; 536/23.2; 536/23.5; 536/24.3; 536/24.31; 536/24.32; 536/24.33
(58) Field of Search .............................. 435/6, 91.2, 91.1, 435/91.21; 536/23.1, 24.3, 24.31, 24.32, 24.33, 232, 23.5

(56) References Cited

U.S. PATENT DOCUMENTS 6,090,556 * 7/2000 Kato ......................................... 435/6

FOREIGN PATENT DOCUMENTS 10337200 12/1988 (JP).

OTHER PUBLICATIONS

Kato K. Adapter–tagged competitive PCR: A novel method for measuring relative gene expression. Nucleic acids Research, vol. 25, No. 22, pp. 4694–4696, Nov. 1997.*

The 21st Annual Meeting of the Molecular Biology Society of Japan Dec. 16 to Dec. 19, 1998, Abstract of Paper P–547 "Mutiplex Adaptor–Tag Competitive PCR," Ryo Matoba et al.

* cited by examiner

Primary Examiner—Stephanie Zitomer
Assistant Examiner—Cynthia B. Wilder
(74) Attorney, Agent, or Firm—Lorusso & Loud (57) ABSTRACT

The present invention provides a method of detecting RNA, comprising: (a) preparing cDNA to be measured and standard cDNA by reverse transcription of RNA as the subject of detection and standard RNA respectively; (b) adding different adapters respectively to the standard cDNA prepared at stepwise concentrations; (c) adding an adapter other than said adapters to the cDNA to be measured; (d) mixing and amplifying the adapter-tagged cDNAs obtained in the steps (b) and (c); (e) measuring the amount ratio of the cDNA measured to the standard cDNA; and (f) detecting said RNA from the measurement results.

10 Claims, 6 Drawing Sheets

CHAIN LENGTH (NUMBER OF NUCLEOTIDES)

EXPRESSION RATIO

```
                              SEQUENCE LISTING

<160> NUMBER OF SEQ ID NOS: 14

<210> SEQ ID NO 1
   <211> LENGTH: 27
   <212> TYPE: DNA
   <213> ORGANISM: Artificial Sequence
   <220> FEATURE:
   <223> OTHER INFORMATION: Synthetic DNA

<400> SEQUENCE: 1
gatccgcgtt ctaacgacaa tatgtac                                         27

<210> SEQ ID NO 2
   <211> LENGTH: 23
   <212> TYPE: DNA
   <213> ORGANISM: Artificial Sequence
   <220> FEATURE:
   <223> OTHER INFORMATION: Synthetic DNA

<400> SEQUENCE: 2
gtacatattg tcgttagaac gcg                                             23

<210> SEQ ID NO 3
   <211> LENGTH: 31
   <212> TYPE: DNA
   <213> ORGANISM: Artificial Sequence
   <220> FEATURE:
   <223> OTHER INFORMATION: Synthetic DNA

<400> SEQUENCE: 3
gatctcttag cgttctaacg acaatatgta c                                    31

<210> SEQ ID NO 4
   <211> LENGTH: 27
   <212> TYPE: DNA
   <213> ORGANISM: Artificial Sequence
   <220> FEATURE:
   <223> OTHER INFORMATION: Synthetic DNA

<400> SEQUENCE: 4
gtacatattg tcgttagaac gctaaga                                         27

<210> SEQ ID NO 5
   <211> LENGTH: 34
   <212> TYPE: DNA
   <213> ORGANISM: Artificial Sequence
   <220> FEATURE:
```

<223> OTHER INFORMATION: Synthetic DNA

<400> SEQUENCE: 5
gatccacgat tagcgttcta acgacaatat gtac					34

<210> SEQ ID NO 6
<211> LENGTH: 30
<212> TYPE: DNA
<213> ORGANISM: Artificial Sequence
<220> FEATURE:
<223> OTHER INFORMATION: Synthetic DNA

<400> SEQUENCE: 6
gtacatattg tcgttagaac gctaatcgtg					30

<210> SEQ ID NO 7
<211> LENGTH: 37
<212> TYPE: DNA
<213> ORGANISM: Artificial Sequence
<220> FEATURE:
<223> OTHER INFORMATION: Synthetic DNA

<400> SEQUENCE: 7
gatcgagcac tcttagcgtt ctaacgacaa tatgtac					37

<210> SEQ ID NO 8
<211> LENGTH: 33
<212> TYPE: DNA
<213> ORGANISM: Artificial Sequence
<220> FEATURE:
<223> OTHER INFORMATION: Synthetic DNA

<400> SEQUENCE: 8
gtacatattg tcgttagaac gctaagagtg ctc					33

<210> SEQ ID NO 9
<211> LENGTH: 41
<212> TYPE: DNA
<213> ORGANISM: Artificial Sequence
<220> FEATURE:
<223> OTHER INFORMATION: Synthetic DNA

<400> SEQUENCE: 9
gatcctaagc taccagttag cgttctaacg acaatatgta c					41

<210> SEQ ID NO 10
<211> LENGTH: 37
<212> TYPE: DNA
<213> ORGANISM: Artificial Sequence
<220> FEATURE:
<223> OTHER INFORMATION: Synthetic DNA

<400> SEQUENCE: 10
gtacatattg tcgttagaac gctaactggt agcttag					37

<210> SEQ ID NO 11
<211> LENGTH: 44
<212> TYPE: DNA
<213> ORGANISM: Artificial Sequence
<220> FEATURE:
<223> OTHER INFORMATION: Synthetic DNA

<400> SEQUENCE: 11
gatcagcgtt agagccttta gtgcgttcta acgacaatat gtac					44

```
<210> SEQ ID NO 12
<211> LENGTH: 40
<212> TYPE: DNA
<213> ORGANISM: Artificial Sequence
<220> FEATURE:
<223> OTHER INFORMATION: Synthetic DNA

<400> SEQUENCE: 12
gtacatattg tcgttagaac gcactaaagg ctctaacgct                              40

<210> SEQ ID NO 13
<211> LENGTH: 22
<212> TYPE: DNA
<213> ORGANISM: Artificial Sequence
<220> FEATURE:
<223> OTHER INFORMATION: Synthetic DNA

<400> SEQUENCE: 13
gtacatattg tcgttagaac gc                                                22

<210> SEQ ID NO 14
<211> LENGTH: 20
<212> TYPE: DNA
<213> ORGANISM: Artificial Sequence
<220> FEATURE:
<223> OTHER INFORMATION: Synthetic DNA

<400> SEQUENCE: 14
atgacaaatt accacatgga                                                   20
```

SEQUENCE LISTING FREE TEXT

SEQ ID NO:1: Synthetic DNA
SEQ ID NO:2: Synthetic DNA
SEQ ID NO:3: Synthetic DNA
SEQ ID NO:4: Synthetic DNA
SEQ ID NO:5: Synthetic DNA
SEQ ID NO:6: Synthetic DNA
SEQ ID NO:7: Synthetic DNA
SEQ ID NO:8: Synthetic DNA
SEQ ID NO:9: Synthetic DNA
SEQ ID NO:10: Synthetic DNA
SEQ ID NO:11: Synthetic DNA
SEQ ID NO:12: Synthetic DNA
SEQ ID NO:13: Synthetic DNA
SEQ ID NO:14: Synthetic DNA

METHOD FOR DETERMINING THE DETECTION VALUE OF A TARGET RNA

BACKGROUND OF THE INVENTION

1. Field of the Invention

The present invention relates to a method of detecting RNA and in particular to a method of detecting RNA, in which RNA can be detected highly accurately.

2. Description of the Related Art

In order to determine the level of gene expression, generally, Northern hybridization is carried out. For the routine determination at the laboratory level, the presence of 5 pg (picograms) of RNA is sufficient for detection. However, in cases where the amount of expression of a target gene is extremely small, 0.3–3 µg of mRNA is required for detection. Thus, it is difficult to apply Northern hybridization to cases where samples of only limited amounts are available (e.g., clinical samples).

Polymerase chain reaction (PCR) is a technique by which DNA or RNA can be detected most sensitively compared to other techniques. However, quantitative determination of gene expression by PCR involves a control experiment in which a calibration curve is prepared using, as the so-called "internal control", a DNA fragment having an amplification efficiency similar to that of a target molecule. Thus, operations are complicated. Furthermore, in order to perform quantitative PCR with a number of genes, it is necessary to prepare a calibration curve for each of the target genes to be quantitatively determined. Thus, a study of genes or a genetic diagnosis with this method requires much time and labor.

SUMMARY OF THE INVENTION

It is an object of the present invention to provide (1) a method of detecting RNA, (2) a method of detecting RNA in which RNA can be detected highly accurately, and (3) a method of detecting RNA in which a small quantified amount of a sample can also be detected and a number of samples can be easily quantified.

As a result of intensive and extensive research toward the solution of the problems described above, the present inventors have found that a target RNA can be detected highly accurately by adding a different adapter to each of RNA-derived cDNA as the subject of detection and cDNAs used for preparing a. standard curve, and then performing PCR. Thus, the present invention has been achieved.

That is, the present invention relates to a method of detecting RNA, comprising:

(a) preparing cDNA to be measured and standard cDNA by reverse transcription of RNA as the subject of detection and standard RNA respectively, (b) adding different adapters respectively to the standard cDNA prepared at stepwise concentrations, (c) adding an adapter other than said adapters to the cDNA to be measured, (d) mixing and amplifying the adapter-tagged cDNAs obtained in the steps (b) and (c), (e) measuring the ratio of the a target cDNA to the amount of standard cDNA, and (f) detecting said RNA from the measurement results.

The different adapters include those containing nucleotides which are different in length from one another. The amplification includes that using an adapter primer and a gene-specific primer.

BRIEF DESCRIPTION OF THE DRAWINGS

The meanings of symbols are as follows: 1, common sequence; 2, cohesive end sequence; 3, spacer sequence; 4, cDNA to be measured; 5, adapter primer; 6, gene-specific primer; 7, streptoavidin; 8, magnetic bead; and 9, label.

DETAILED DESCRIPTION OF THE INVENTION

Hereinafter, the present invention will be described in detail.

The present invention relates to a method of detecting RNA, in which cDNA (referred to as "standard cDNA") synthesized from "RNA used as the control (referred to as "standard RNA", which are used for preparing a standard curve) are mixed with cDNA as the subject of measurement (referred to as "cDNA to be measured") synthesized from target RNA as the subject of detection (referred to as "detection target RNA"), and these cDNAs are amplified in the same reaction system whereby the amount ratio of the cDNA to be measured to the standard cDNA is determined, and the measurement result is used as the indication for detecting the RNA.

For the detection of gene expression by PCR, a control experiment should be conducted where in a reaction system, a calibration curve is prepared using, as an internal control, a DNA fragment having the same amplification efficiency as that of the target molecule. If this operation can be performed in a single reaction tube containing the target molecule, the detection result of the target molecule can be obtained easily with less errors.

To allow the target DNA to be accurately and easily measured in a reaction in a single test tube, the present inventors have added a different adapter to each of DNAs to be amplified, whereby the amplified DNAs can be distinguished from one another. Hereinbelow, each step in the method of the present invention is described.

(1) Preparation of RNA and cDNA

The RNA as the object of detection (detection target RNA) includes RNAs derived from various organs. However, the type of RNA is not limited. The detection target RNA may be 1 or more kinds of RNA, preferably 1 to 5 kinds of RNA. If 2 or more kinds of RNA are used, these may be those derived from different tissues or cells or the same tissues or cells. For example, RNAs which are of the same kind but different in the stage (e.g. at several days after birth, at several weeks or several years after birth) can be selected as the target detection RNA.

On one hand, RNA (standard RNA) is a different kind from the target detection RNA, and it should be selected to be suited for the target detection RNA. Accordingly, if the target detection RNA is derived from e.g. a cerebellum extract, standard RNA may be derived from a whole-brain (cerebrum, interbrain, midbrain and medulla bulb) extract excluding the cerebellum.

The detection target RNA and standard RNA described above are used to synthesize their corresponding cDNAs by use of reverse transcriptase, and the cDNA to be measured and standard cDNA are thus obtained. Both the cDNA measured and standard cDNA can be prepared by any methods known in the art. For example, a technique of preparing poly(A)$^+$ RNA from cells of various organs or tissues and converting the RNA into cDNA with reverse transcriptase (Gubler, U and Hoffman, B. J., Gene, 25, 263–269 (1983); Okayama, H. and Berg. P., Mol. Cell. Biol., 18, 5294 (1982)) Alternatively, cDNA may be synthesized using a commercial kit (cDNA synthesis kit, Lifetech Oriental Co., Ltd.).

The cDNA population obtained after the cDNA synthesis described above contains not only the target genes used as the target cDNA and standard cDNA but also cDNAs not corresponding to the target genes. Accordingly, the target genes only in the above cDNAs are amplified in the present invention by the adapter-tagging reaction and PCR reaction using specific primers (e.g. an adapter primer and a gene-specific primer) described below, and the amount ratio thereof can thus be determined.

(2) Preparation of the Adapters

As described above, the present invention is characterized by DNAs each having a different adapter added thereto measured all at once in the same reaction system, that is, in the same reaction tube. Each different adapter is designed such that upon amplification, a certain DNA can be distinguished from other DNAS, and this adapter refers to a double-stranded oligonucleotide capable of ligation to the double-stranded cDNA to be measured. Insofar as adapters can distinguish amplification fragments from one another, the type of the adapters is not limited, and examples of such adapters include those having an oligonucleotide different in length.

Although the number (kind) of adapters which can be used in the same reaction system is not particularly limited in the present invention, 6 or 7 or less kinds of adapters are preferablyused. Accordingly, the kinds of adapters tobe added to the standard cDNA and the kind of adapter to be added to the cDNA to be measured can be suitably selected within the kinds of adapters used. For example, if one kind of cDNA is to be measured, one kind of adapter is added to the cDNA to be measured. On one hand, it is necessary to obtain at least 2 data in order to prepare a standard curve, the standard cDNA should be prepared at 2 or more concentrations. Accordingly, at least 3 kinds of adapters should be used. If the preferable number (6 to 7) of adapters is used, up to 5 or 6 adapters can be added to standard cDNA (that is, the standard cDNA can be prepared at 5 or 6 or less concentrations).

If 3 kinds of cDNAs are to be measured in the same manner as described above, 3 kinds of adapters should be added to the cDNAs to be measured, and e.g. 3 or 4 kinds of adapters can be added to standard DNA (that is, the standard DNA can be prepared at 3 or 4 or less concentrations).

Figure 1:
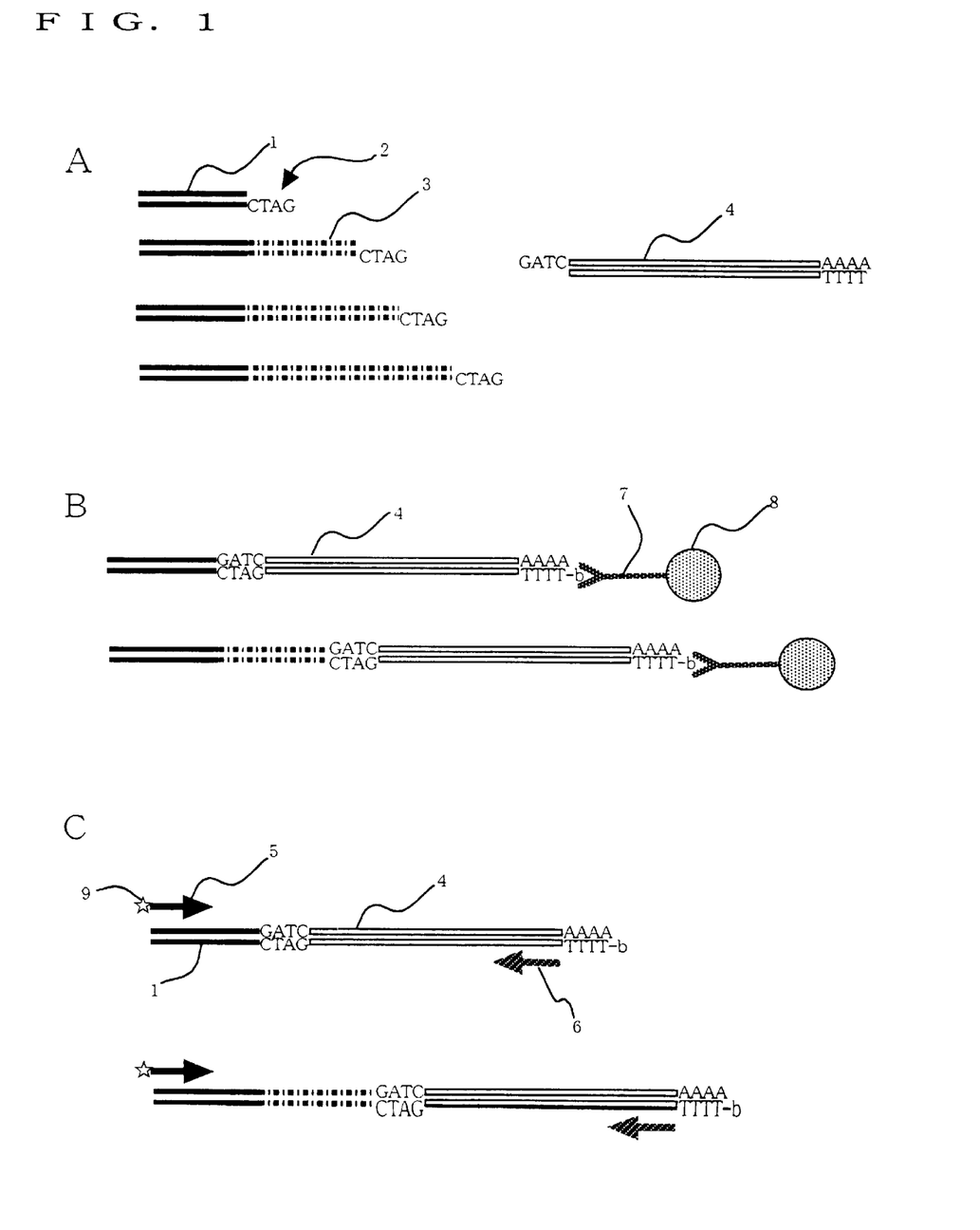
FIG. 1 is a schematic illustration of the adapters used in the present invention.

Each adapter used in the present invention is composed of (1) sequence (called cohesive end sequence) of a protruded single-stranded end capable of annealing with the cohesive end (obtained by restriction enzyme treatment) of cDNA, (2) sequence (called spacer sequence) which is different in length for each adapter, and (3) sequence (called common sequence) in common with each adapter, and the cohesive end sequence, the spacer sequence and the common sequence are linked in this order (the spacer sequence and the common sequence are double-stranded) (FIG. 1).

In FIG. 1A, the cohesive end sequence 2 can be suitably designed depending on the type of restriction enzyme used for producing suitable-length fragments of cDNA obtained from RNA through reverse transcription. Further, the common sequence 1 and the spacer sequence 3 can also be arbitrarily designed. The spacer sequence may have not only a different length of oligonucleotide but also a different oligonucleotide sequence in each adapter used. However, the spacer sequence 3 may or may not be inserted into the shortest adapter.

In the present invention, the minimum length of common sequence 1 is 20 to 30 nucleotides. Accordingly, the sequence of the spacer can be changed to produce a wide variety of adapters having a varying length (FIG. 1A). For example, when 6 kinds of adapters are used, the length of the minimum adapter is 20 to 30 nucleotides, and size difference between adjacent adapters are 2 to 4 nucleotides whereby an adapter having 20 nucleotides excluding the cohesive end sequence can constructed as that having the shortest sequence, and an adapter having 32 to 54 nucleotides excluding the cohesive end sequence as that having the longest sequence. As a result, adapters each having a different length depending on the length of the spacer can be obtained, and the PCR products described below can thereby be distinguished from one another.

These adapters can be obtained in any known methods, for example by chemical synthesis with a DNA synthesizer from Perkin-Elmer.

The number of adapters, the number of oligonucleotides etc. described above are not intended to limit the scope of the present invention.

(3) Addition of Adapters

Then, a different adapter is added to each cDNA to be measured. Similarly, a different adapter is added to each standard cDNA.

In the present invention, an excess of adapters can be mixed with each sample so that the sample is not deficient in the adapter added to the cDNA to be measured. In this case, one of both a certain specific substance and another substance specifically reacting with said substance (e.g. an antibody and its antigen, an enzyme and its substrate, and streptoavidin and biotin) is preferably added to cDNAs in each sample so that the excessively mixed adapters can be removed, that is, only the sample to which the adapters were bound can be recovered. If one of the above 2 substances is immobilized on the solid support, only the cDNAs to which the adapters were added can be recovered by the specific reaction between the 2 substances (FIG. 1B). In FIG. 1B, biotin (i.e. "-b" at the terminal of cDNA), streptoavidin 7, and magnetic bead 8 for facilitating recovery are illustrated.

However, if the amount of RNA as the starting material is large, the relative difference between the amount of cDNA obtained by reverse transcription of RNA and the amount of the free adapter is considered to be small. In this case, because it is not necessary to remove the adapter, addition of the above-specified substance may be omitted.

Figure 2:
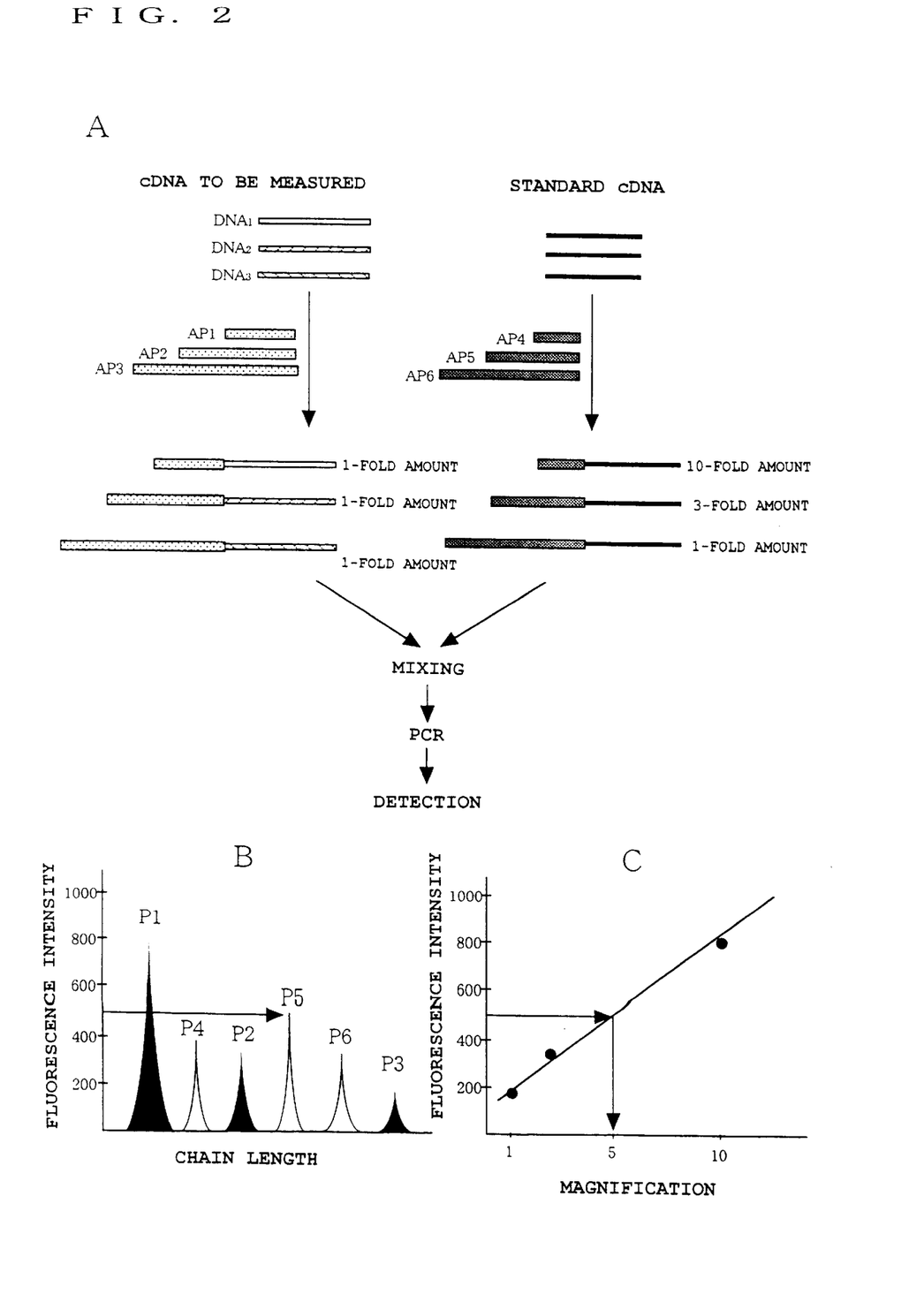
FIG. 2 shows an outline of the detection method of the present invention.

The step of ligating the adapter to the cDNA to be measured, and the subsequent steps, are described below using 3 kinds of cDNAs ($DNA_1$, $DNA_2$ and $DNA_3$) and one kind of standard cDNA (FIG. 2).

Adapters (having different lengths, designated $AP_1$, $AP_2$ and $AP_3$) are added to the cDNAs measured, that is, $DNA_1$, $DNA_2$ and $DNA_3$ and they can be distinguished by difference of adapter length.

The cDNA measured, to which the adapter had been added, is prepared in the 1-fold amount (FIG. 2A).

On the other hand, the standard cDNA is prepared at stepwise concentrations, and different kinds of adapters are added to the DNA at different concentrations. For example, in FIG. 2, adapters AP4, AP5 and AP6 which are different in length from each other are added to the standard cDNAs prepared stepwise in 10-, 3- and 1-fold amounts. However, the concentrations of DNA are not limited to the ratio of 10:3 1 described above, and the best conditions can be selected for preparing the standard curve. Accordingly, if 3 kinds of adapters are used, their concentrations can be set arbitrarily at e.g. 1:10:100 or 1:5:25. The "1-fold amount" refers to the standard amount for preparing stepwise concentrations.

(4) Mixture and Amplification

The respective cDNAs described above are mixed in a reaction tube, and amplification reaction (PCR) is conducted with said cDNAs as templates and by use of an adapter primer and a gene-specific primer.

The adapter primer refers to an oligonucleotide having a complementary sequence to the sequence of the adapter used in the present invention and being capable of hybridizing with said adapter (FIG. 1C). However, at least 15 nucleotides in the sequence of the adapter primer should hybridize with the common sequence. In FIG. 1C, the nucleotide sequence of the adapter primer 5 can be arbitrarily designed and synthesized depending on the sequence of the common sequence 1 in the adapter. In this case, the length of the nucleotide sequence of the above adapter primer 5 is 15 to 50 nucleotides, preferably 25 to 30 nucleotides. The adapter primer 5 to be hybridized is designed to hybridize with the longer strand of the double strands of the adapter.

In the present invention, the adapter primer is preferably labeled with suitable label 9 so that the amplification product by PCR can be detected by a detector (FIG. 1C). The labeling substance of label 9 includes fluorescein, rhodamine etc. for fluorescent labeling and $^{32}P$, $^{35}S$ etc. for labeling with a radioactive substance, and labeling of the primers with these labeling substances can be performed in any method known in the art.

On one hand, the gene-specific primer refers to an oligonucleotide having a complementary sequence to the sequence of cDNA4 to be measured and being capable of hybridizing with it (FIG. 1C). The length of the nucleotide sequence of the gene-specific primer 6 is 15 to 50 nucleotides, preferably 25 to 30 nucleotides.

The PCR conditions can be suitably altered depending on cDNA to be amplified. For example, the conditions for amplification are: 90 to 98° C. for 15 seconds to 1 minute, preferably 94° C. for 20 seconds for the denaturation step; 37 to 72° C. for 15 seconds to 1 minute, preferably 50° C. for 40 seconds for the annealing step; and 50 to 75° C. for 15 seconds to 1 minute, preferably 72° C. for 40 seconds for the extension step; and this cycle is repeated, and 30 to 40 cycles, preferably 35 cycles, are thus conducted. However, when Taq Gold (Perkin-Elmer) is used, the activation step at 95° C. for 10 minutes is preferably added before the above amplification cycle, and the extension step at 72° C. for 10 to 30 minutes can be added after the amplification cycle, so that non-extended fragments in the amplified DNAs can be completely extended. Further, the amplification product can also be cryopreserved (e.g. −20° C.) so that its measurement can be conducted on another day.

(5) Detection

Detection of the resulting amplification product can be performed using various methods. For example, if the primer used in PCR is previously labeled with a fluorescent pigment etc., it can be detected as fluorescence intensity, and if it is labeled with a radioactive substance, it can be detected by a densitometer after exposure to an X-ray film.

Alternatively, the amplificationproduct maybe subjected to agarose gel electrophoresis, polyacrylamide gel electrophoresis and stained with ethidium bromide, SYBR Green etc., to measure the density of the amplification product band.

If a different kind of adapter is ligated (tagged) to each group of standard cDNA prepared at stepwise different concentrations, the standard cDNAs onto which the adapter was tagged can be distinguished for each fragment depending on the kind of adapter in the measurement step after PCR. In the method of the present invention, a standard curve (e.g. mathematical function such as linear function, secondary function etc.) is prepared on the basis of the measurement value of each of the standard cDNA groups, and the amount ratio to the standard cDNA is determined by extrapolation of the measurement value of the cDNA measured in this standard curve.

The amplification product can be measured in a predetermined measuring apparatus (e.g. Sequencer manufactured by Perkin-Elmer). In FIG. 2, when the measurement results (fluorescence intensity) of standard cDNA prepared in 10-, 3-, and 1-fold amounts are expressed respectively as P1, P2 and P3 (black peaks in FIG. 2B) which appear at different peak positions depending on the difference of the length of the adapter chain, the standard curve can be expressed as shown in FIG. 2C. Because the calibration curve in FIG. 2C can be drawn as linear function, the relative amount of the cDNA measured to the standard cDNA can be known by substituting the fluorescence intensity of the cDNA measured in the formula of said function. For example, in FIG.

2, if the fluorescence intensity of $DNA_2$ is 500 (P5 in FIG. 2B), the magnification is 5 according to FIG. 2C. Accordingly, it can be known that DNA, as the cDNA to be measured is expressed in a 5-fold excess amount compared to the standard cDNA. If the absolute amount of mRNA derived from gene in DNA is known, the absolute amount of the cDNA to be measured can be known, and if the absolute amount of mRNA is not known, the relative ratio of expression can be determined.

Finally, the measurement results obtained as described above are used as the indication to determine the ratio of the expression amount of the RNA for gene in the tissues used as the sample.

2. Analysis of gene expression pattern by the method of the invention:

According to the method of the present invention, the RNA as the object of detection can be detected accurately, so when the expression pattern of the same kind of gene is detected at each development stage of the individual, the expression pattern of various genes can be analyzed. For example, when the expression level of a certain gene in a mouse is measured at several days after birth, around 10 days after birth, and after several weeks after birth, the expression level of gene may be increased or decreased as the mouse grows. Otherwise, the expression amount of gene may be constant regardless of the development stage. Accordingly, gene can be classified into several groups according to the mode of these expression patterns.

Further, by detecting the expression patterns of genes from healthy persons and the expression patterns of genes from a patient with a certain disease, it can be judged which gene has changed.

DETAILED DESCRIPTION OF PREFERRED EMBODIMENTS

Hereinafter, the present invention is described in more detail by reference to the Examples. However, the technical scope of the present invention is not limited to the Examples.

EXAMPLE 1:

Detection of RNA for ATP Synthase Coupling Factor Gene

The object of this example is to detect RNA for ATP synthase coupling factor gene.

The objective mouse cerebellum tissue-derived RNA was extracted with trizole (Gibco-BRL) etc. 3 μg total RNA and 1.5 pmol of 5'-biotinylated oligo-dT were dissolved in 11 μl distilled water. Then, the mixture was heated at 70° C. for 5 minutes and cooled to room temperature.

Then, cDNA was synthesized from the RNA.
(1) Synthesis of First Strand cDNA

| Reaction solution composition for synthesis of cDNA | |
| --- | --- |
| 0.1 M DTT | 2 μl |
| 5 × reaction buffer (Gibco-BRL) | 4 μl |
| 10 mM dNTP | 1 μl |
| Rnase inhibitor | 1 μl |

After the reaction solution with the composition described above was heated at 42° C. for 2 minutes, 1 μl of 200 units/μl Superscript II was added. After heated at 37° C. for 30 minutes, the mixture was heated at 42° C. for 30 minutes. After transferred onto ice, the following reagents for synthesis of second strand cDNA were added.

(2) Synthesis of Second Strand cDNA

| Reaction solution composition for synthesis of cDNA | |
| --- | --- |
| 10 × buffer for synthesis of second strand | 10 μl |
| 10 mM dNTP | 4 μl |
| 100 mM DTT | 2 μl |
| E. coli DNA ligase | 2 μl (20 units) |
| E. coli DNA polymerase I | 4 μl (40 units) |
| E. coli RNase H | 1 μl (2 units) |
| Total amount (adjusted with distilled water) | 100 μl |

The above reaction solution was kept at 16° C. for 2 hours and then heated at 70° C. for 30 minutes whereby the enzymes were inactivated. 40 μl of the above reaction solution was transferred to a new tube.

(3) Cleavage with a Restriction Enzyme

| Composition for the reaction solution | |
| --- | --- |
| 10 × K buffer(TaKaRa Inc.) | 10 μl |
| The above cDNA solution | 40 μl |
| Mbo I | 10 units |
| Total amount (adjusted with distilled water) | 100 μl |

The above reaction solution was treated at 37° C. for 30 minutes to cleave the cDNA.

Then, the cDNA fragment was extracted with phenol/chloroform and extracted with ethanol. The cDNA was rinsed twice with 70% ethanol and dissolved in 500 μl of 0.1×TE buffer.

(4) Adapter-tagging Reaction

| Composition for the reaction solution | |
| --- | --- |
| 10 × T4 ligase buffer | 7.5 μl |
| 10 pmol/μl MA-1L adapter | 7.5 μl |
| 10 pmol/μl MA-1S adapter | 7.5 μl |
| T4 DNA ligase | 350 units (TaKaRa) |
| The above Mbo I-cleaved cDNA | 50 μl |
| Total amount (adjusted with distilled water) | 75 μl |

"L" and "S" in the adapter names MA-1L and MA-1S mean long and short chains of each adapter respectively.

The above reaction solution was kept at 16° C. overnight.

The oligonucleotide sequences of the adapter and the adapter primer are as follows:

| Adapter | Sequence | |
|---|---|---|
| MA-1L: | 5'-GATCCGCGTTCTMCGACMTATGTAC-3' | (SEQ ID NO: 1) |
| S: | 3'-GCGCMGATTGCTGTTATACATG-5' | (SEQ ID NO: 2) |
| MA2-2L: | 5'-GATCTCTTAGCGTTCTMCGACAATATGTAC-3' | (SEQ ID NO: 3) |
| S: | 3'-AGMTCGCMGATTGCTGTTATACATG-5' | (SEQ ID NO: 4) |
| MA-3L: | 5'-GATCCACGATTAGCGTTCTMCGACAATATGTAC-3' | (SEQ ID NO: 5) |
| S: | 3'-GTGCTMTCGCMGATTGCTGTTATACATG-5' | (SEQ ID NO: 6) |
| MA-4L: | 5'-GATCGAGCACTCTTAGCGTTCTMCGACAATATGTAC-3' | (SEQ D NO: 7) |
| S: | 3'-CTCGTGAGMTCGCAAGATTGCTGTTATACATG-5' | (SEQ ID NO: 8) |
| MA-5L: | 5'-GATCCTMCCTACCAGTTAGCGTTCTMCGACMTATGTAC-3' | (SEQ ID NO: 9) |
| S: | 3'-GATTCGATGGTCMTCGCMGATTGCTGTTATACATG-5' | (SEQ ID NO: 10) |
| MA-6L: | 5'-GATCAGCGTTAGAGCCTTTAGTGCGTTCTMCGACAATATGTAC-3' | (SEQ ID NO: 11) |
| S: | (SEQ ID NO: 12) 3'-TCGCAATCTCGGMATCACGCMGATTGCTGTTATACATG-5' | |

FAM (5-carboxyfluorescein) labled CIS adapter primer
5'-GTACATATTGTCGTTAGAACGC-3'                                       (SEQ ID NO: 13)

In this example, cDNA derived from the whole brain from a matured mouse from which the cerebellum had been removed was used. Adapter MA-6, MA-3 or MA-1 was bound to this cDNA, and 3 kinds of adapter-tagged cDNA were prepared.

On one hand, the detection target used was cDNA derived from the cerebellum from the above mouse, and MA-2 was ligated to cDNA at 4 days after birth, MA-4 to cDNA at 12 days after birth, and MA-5 to cDNA at 6 weeks after birth.

After the tagging reaction of the adapters, 25 μl of 5 M NaCl was added, and 20 μl of 10 mg/ml streptoavidin-covered paramagnetic beads were added, and these were adsorbed on ice.

Then, the cDNAs derived from the whole brain minus cerebellum(hereinafter referred as "whole brain"), as well as the cDNAs derived from the cerebellum at 4 days, 12 days and 6 weeks after birth, were prepared in the amounts described below and these cDNAs were mixed. As the standard cDNAs, MA-6 was ligated to the cDNA a 1-fold amount of the cDNA, MA-3 to the cDNA in a 3-fold amount of the cDNA, and MA-1 to the cDNA in a 10-fold amount of the cDNA. Further, the detection target used was the cDNAs derived from the cerebellum at 4 days, 12 days and 6 weeks after birth, and any of them were used in a 1-fold amount of the cDNA.

| | |
|---|---|
| Whole brain-derived cDNA (with ligated MA-1) | 30 μl |
| Whole brain-derived cDNA (with ligated MA-3) | 9 μl |
| Whole brain-derived cDNA (with ligated MA-6) | 3 μl |
| Cerebellum-derived cDNA at 4 days after birth (with ligated MA-2) | 3 μl |
| Cerebellum-derived cDNA at 12 days after birth (with ligated MA-4) | 3 μl |
| Cerebellum-derived cDNA at 16 weeks after birth | 3 μl |

-continued

| |
|---|
| (with ligated MA-5) |

The beads were washed with 120 μl distilled water, and 120 μl distilled water was suspended in. 2.1 μl aliquot was pipetted into each well on a 96-well microtiter plate, and 0.4 μl (10 pmol/μl) gene-specific primer (primer specific for ATP synthase coupling factor gene) was added.

The sequence of the gene-specific primer (the primer is the same for both the cerebellum-derived and whole brain-derived cDNA):

5'-ATGACAAATTACCACATGGA-3' (SEQ ID NO: 14)

Then, 2.5 μl of 2×Taq Gold mixture was added (5 μl/sample). The composition for the reaction solution is as follows:

| 2 × Taq Gold mixture | |
|---|---|
| 10 × PCR buffer | 54 μl |
| 20 mM dNTP | 4 μl |
| 10 pmol/μl 6-FAM-C1S | 20 μl |
| Taq Gold | 5 μl (25 units) |
| Total amount (adjusted with distilled water) | 270 μl |

The PCR reaction was conducted under the following conditions. That is, the mixture was incubated at 95° C. for 10 minutes for activation of Taq Gold and then subjected to 40 cycles each consisting of thermal reaction at 94° C. for 20 seconds, at 50° C. for 40 seconds and at 72° C. for 40 seconds. After the reaction, the mixture was kept at 72° C. for 20 minutes.

5 μl T4 mixture was added to the reaction mixture and kept at 37° C. for 2 hours.

| Composition of the T4 mixture | |
|---|---|
| 10 × K buffer | 27 μl |
| T4 DNA polymerase | 20 units |
| Total amount (adjusted with distilled water) | 270 μl |

1 μl of the above T4 mixture was removed, and 7 μl formamide dye was added to it. To this diluted sample was added an equal volume of a marker mix, and the mixture was heated at 95° C. for 3 minutes. After heating, 0.8 μl aliquot was injected to a DNA sequencer (Perkin-Elmer).

Figure 3:
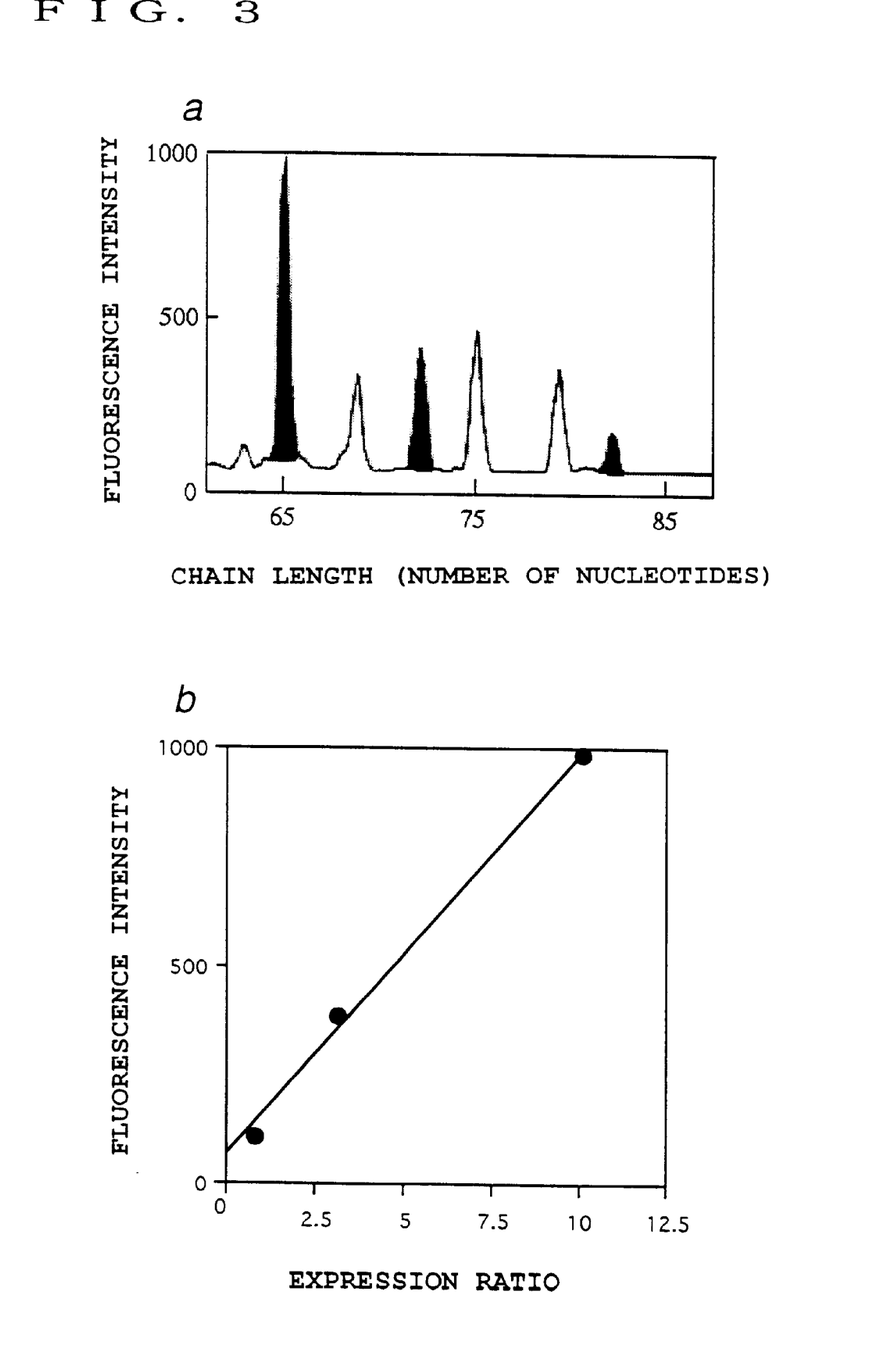
FIG. 3 shows the results of detection of the expression pattern of a mouse cerebellum.

As a result, the peaks of fluorescent density shown in FIG. 3a were obtained. In FIG. 3a, the black peaks refer to the standard cDNA, and the white peaks refer to the DNA derived from the mouse cerebellum. When a standard curve was drawn on the basis of the fluorescence intensity of black peaks, FIG. 3b was obtained. When the cDNAs from the mouse at 4 days, 12 days and 6 weeks after birth were measured on the basis of this standard curve, it was found that they have 2.5-fold, 4-fold and 2.8-fold expression amounts relative to the expression amount of the standard cDNA.

EXAMPLE 2

In this example, 5 genes were examined for the ratio of expression amounts in the same manner as in Example 1. The standard cDNA used was the same whole brain-derived cDNA as in Example 1.

The results are shown in Table 1.

TABLE 1

| | Adapter | | | | | | Coefficient of Correlation |
|---|---|---|---|---|---|---|---|
| | MA-1 | MA-2 | MA-3 | MA-4 | MA-5 | MA-6 | (from standard curve) |
| A | 1609 | 2439 | 325 | 990 | 345 | 85 | 0.988 |
| B | 1930 | 104 | 334 | 301 | 221 | 48 | 0.987 |
| C | 2215 | 451 | 396 | 372 | 432 | 80 | 0.987 |
| D | 379 | 419 | 64 | 301 | 176 | 0 | 0.99 |
| E | 2352 | 141 | 630 | 285 | 120 | 49 | 0.914 |

In Table 1, A indicates the measurement results of a mouse serine/threonine protein kinase DLK gene; B and E, those of unidentified novel genes; C, those of a mouse local adhesive kinase gene; and D, those of a mouse ribosome protein S6 kinase protein (rsk).

In A, MA-2, MA-4 and MA-5 indicate detection results (fluorescence intensity) when adapters MA-2, MA-4 and MA-5 were added respectively to gene, and MA-1, MA-3 and MA-6 indicate detection results (fluorescence intensity) when adapter MA-1 (10-fold amount), MA-3 (3-fold amount) and MA-6 (1-fold amount) were added to the cDNA derived from the mouse whole brain. The correlation coefficients of standard curves of A to E are nearly 1, indicating that correct curves are drawn in any cases.

On the basis of the above results, the ratio of expression amounts in each sample to the whole brain was compared between the case where the ratio was calculated using the standard curve and the case where the whole brain cDNA only to which MA-3 had been added as the standard cDNA was used.

The results are shown in Table 2. In A to E, the upper numbers indicate the ratio of expression amounts obtained using the standard curve, and the lower numbers indicate the ratio calculated using one standard cDNA (MA-3-tagged whole brain cDNA) only. In Table 2, some indicate large scatter between upper numbers and lower numbers (A and D in Table 2), and it was found that by preparing the standard curve, accurate measurement can be obtained.

TABLE 2

| | MA-2 | MA-4 | MA-5 |
|---|---|---|---|
| A | 14.6 | 6.2 | 2.4 |
| | 22 | 9.3 | 3.2 |
| B | 1.2 | 2.1 | 1.7 |
| | 0.93 | 2.7 | 2.0 |
| C | 2.5 | 2.2 | 2.4 |
| | 3.4 | 2.8 | 3.3 |
| D | 10.7 | 7.9 | 5.0 |
| | 20 | 14.8 | 8.3 |
| E | 0.9 | 1.4 | 0.8 |
| | 0.7 | 1.4 | 0.6 |

EXAMPLE 3

Classification of Genes

For 419 DNAs selected from a pool of (about 7000) clone nucleotide sequences extracted at random from a mouse cerebellum cDNA library, their relative expression amounts in 3 samples at 4 days after birth (at the most vigorous stage for granulocyte growth), at 12 days after birth (at the most vigorous stage for granulocyte migration, axon extension and synapse formation), and at 6 weeks after birth (matured body) were measured according to the method of the present invention.

The adapter used was the same as in Example 1, and as standard cDNA, cDNA derived from a mouse whole brain (excluding the cerebellum) was used. Ligation of adapters, PCR and detection were conducted in the same manner as in Example 1. For classification of genes by expression patterns, cluster analysis (Ward's method) was conducted.

Figure 4:
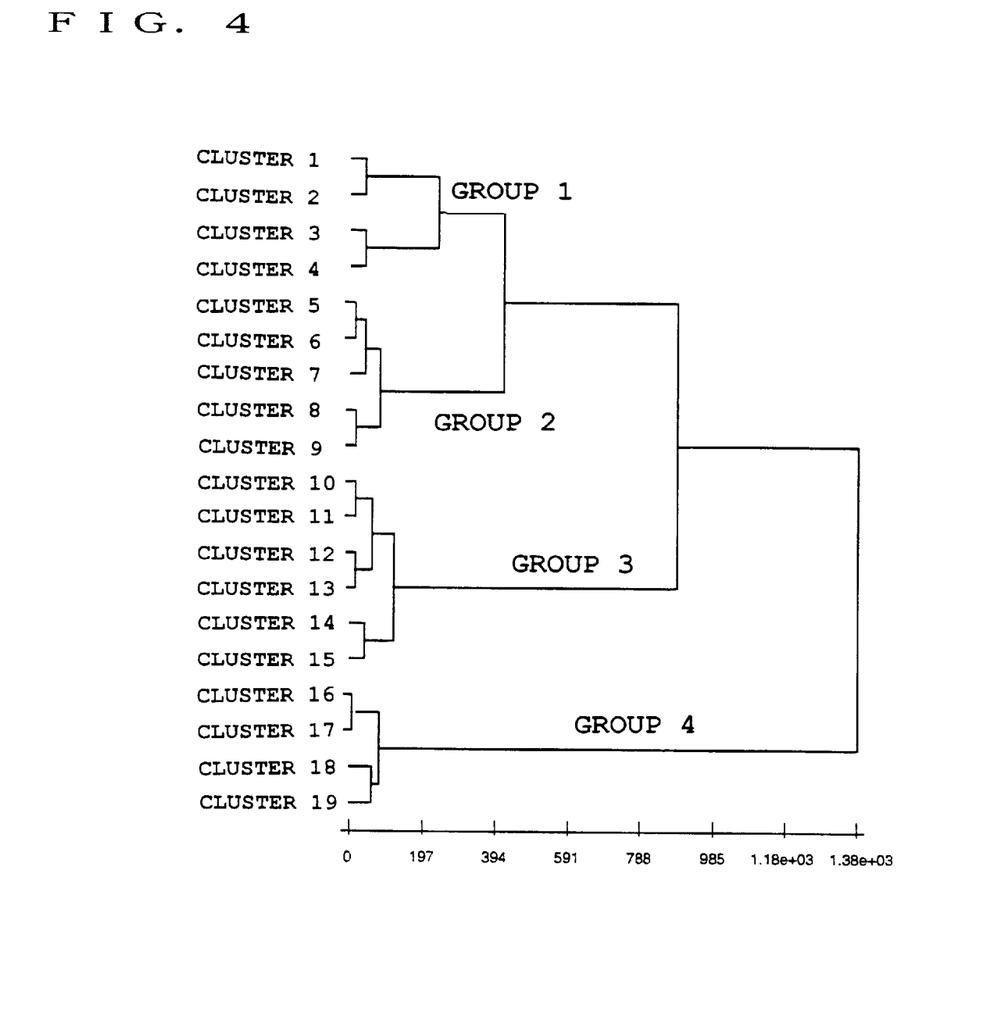
FIG. 4 shows the results of cluster analysis.
Figure 5:
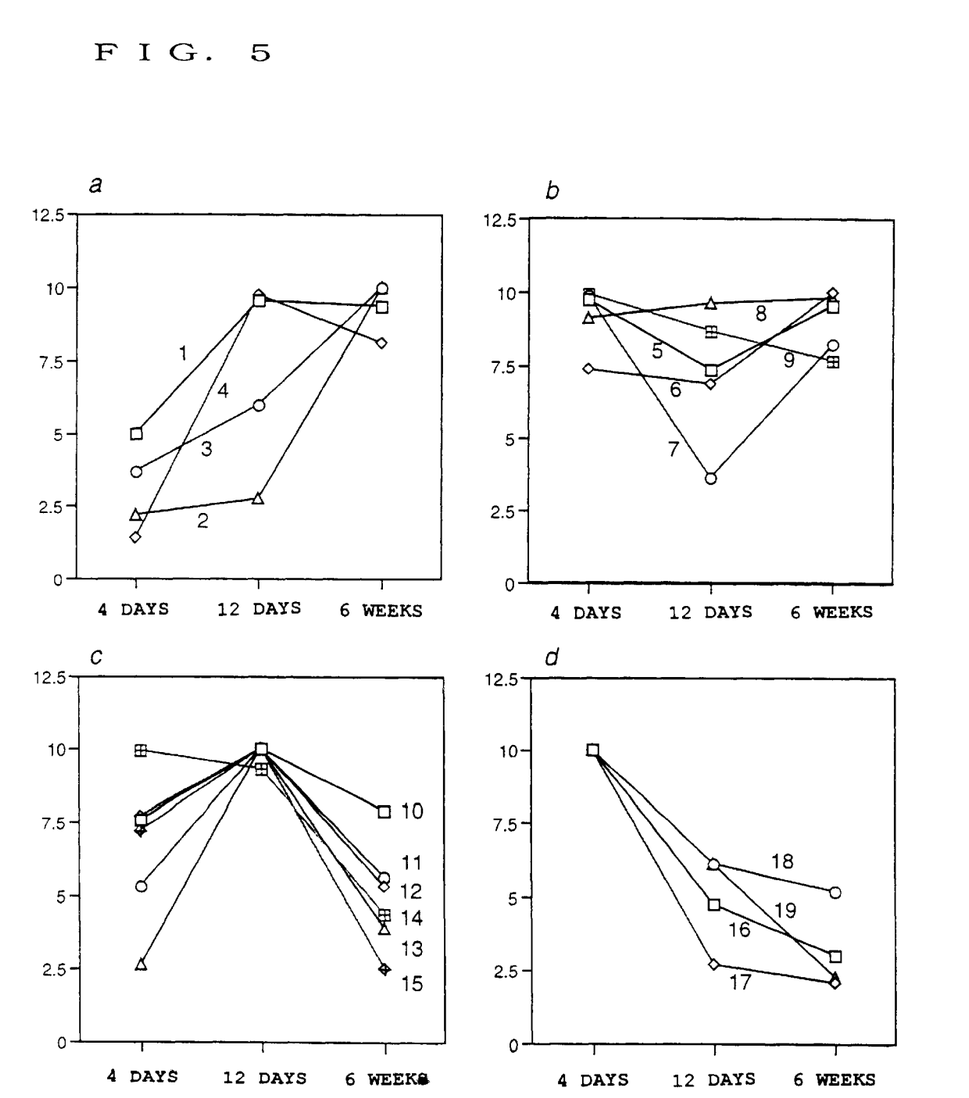
FIG. 5 shows expression patterns of clusters classified into 4 groups.

As a result, 419 genes were classified into 19 clusters. These clusters were classified into 4 large groups (FIG. 4). An expression pattern of each cluster is shown in FIG. 5. In FIG. 5, a shows genes increasing as the mouse grows, b shows genes indicating a nearly constant expression amount regardless of the expression stage, c shows genes indicating a peak of expression at 12 days after birth, and d shows expression patterns of geiles decreasing as the mouse grows. A number assigned to each graph in FIG. 5 corresponds to the number of each cluster in FIG. 4. Accordingly, it is understood that e.g. Group 1 (clusters 1 to 4) in FIG. 4 is a group whose expression amount increases as the mouse grows, as shown in FIG. 5a.

From the above 419 genes, 4 categories of genes, i.e. those coding for protein kinases, those coding for ribosome proteins, those coding for cytoskeletal proteins and those coding for proteins involved in the brain, were selected and examined which group or cluster these genes belong to.

Figure 6:
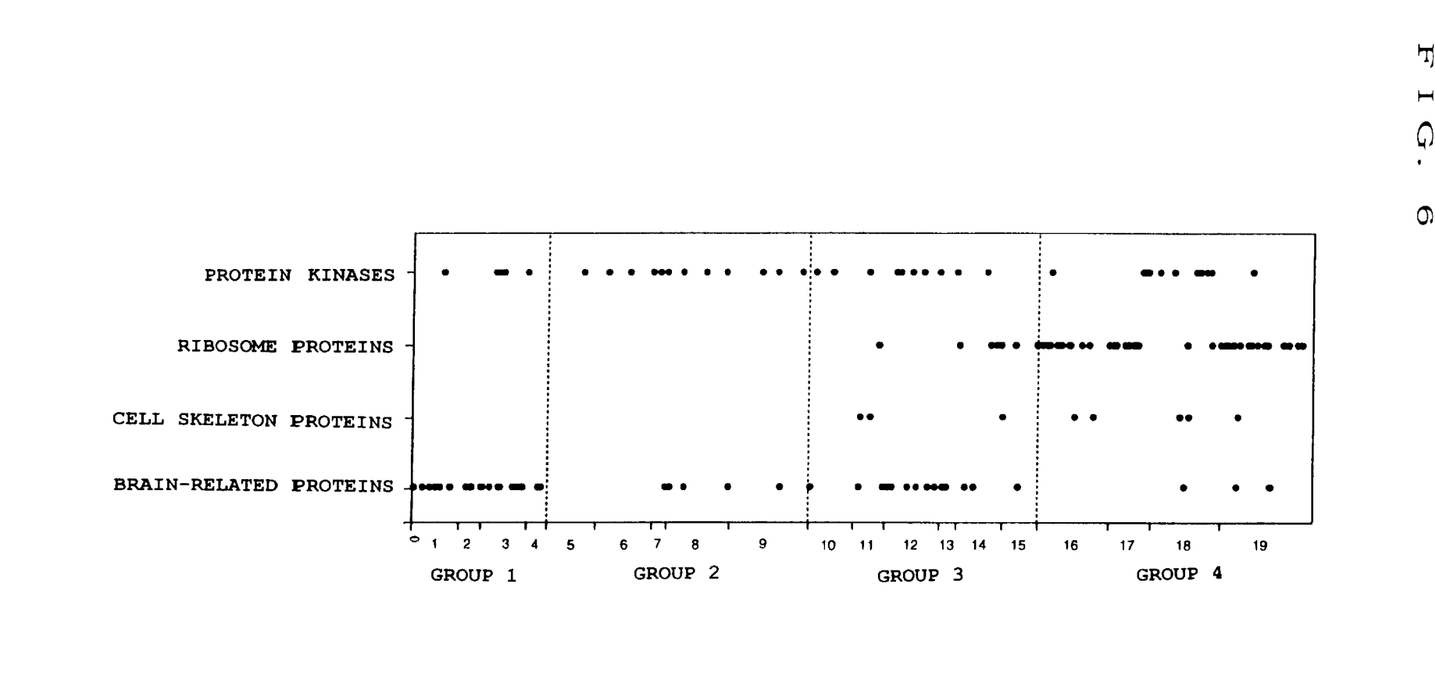
FIG. 6 shows the results of classification of various genes contained in the cerebellum from a mouse after birth.

The results are shown in FIG. 6. For example, the majority of ribosome proteins belongs to the group with a peak at 4 days after birth, whereas genes relating to cell skeleton belong to only groups 3 and 4. On the other hand, there is no characteristic expression pattern in protein kinase.

Further, cerebellum-specific genes are observed only in group 3 with a peak of expression at 12 days and in group 1 with a peak of expression in the matured body. This indicates that the cerebellum-specific expression pattern is closely related to the expression pattern of the development process.

According to the present invention, there is provided a method of detecting RNA. The method of the present invention can detect the expression amount of a target gene highly accurately, and thus it is useful for detection etc. of gene involved in a specific disease.

What is claimed is:

1. A method for determining the detection value of a target RNA comprising:

(a) preparing at least one target cDNA by reverse transcription of the target RNA and a standard cDNA by reverse transcription of a standard RNA;

(b) preparing at least two separate standard samples each containing a different, predefined amount of the standard cDNA and a separate target sample containing an unknown concentration of the target cDNA;

(c) adding different adapters, respectively, to each of the samples in excess of that amount necessary to tag all cDNA present in the sample, to obtain adapter-tagged cDNAs;

(d) mixing the samples containing the adapter-tagged cDNAs to obtain a mixture;

(e) amplifying only the target adapter-tagged cDNA and the adapter-tagged standard cDNA;

(f) obtaining separate measurements for each of the amplified cDNAs;

(g) determining a relationship between the measurements and relative amounts of amplified standard cDNA from the measurements for the amplified cDNA, the measurements for the amplified and adapter-tagged standard cDNA each being different in accordance with the different predefined amounts of the standard cDNA;

(h) applying the measurement for the amplified target cDNA to the determined relationship to obtain a value for the relative amount of the target cDNA; and (i) determining a detection value for the target RNA based on the obtained relative amount value for the target cDNA.

2. The method according to claim 1 wherein the different adapters comprise nucleotides which are different in length from one another.

3. The method according to claim 1 wherein said amplifying is by polymerase chain reaction using an adapter primer and a gene-specific primer.

4. The method according to claim 1 wherein the adapter primer carries a label.

5. The method according to claim 4 wherein the label is fluorescent or radioactive.

6. The method according to claim 1 werein, in step (c), to each sample an amount of adapter in excess of the cDNA contained therein is added and excess adapter not bound to cDNA is subsequently removed from each sample.

7. The method according to claim 1 wherein the separate measurements are obtained as a single, continuous spectrum in step (f), with each of the amplified cDNAs appearing as a separate peak in the spectrum.

8. The method according to claim 1 wherein each adapter used in step (c) is composed of (1) a cohesive end sequence which anneals with a cDNA cohesive end obtained by restriction enzyme treatment, (2) a spacer sequence which is different in length for each adapter, and (3) a common sequence which is the same for all adapters.

9. The method according to claim 8 wherein the spacer sequences differ from each in length by at least 2 nucleotides.

10. The method according to claim 1 wherein the relationship determined in step (g) is a linear relationship.

* * * * *

UNITED STATES PATENT AND TRADEMARK OFFICE
CERTIFICATE OF CORRECTION

PATENT NO. : 6,248,534 B1
DATED : June 19, 2001
INVENTOR(S) : Kato et al.

It is certified that error appears in the above-identified patent and that said Letters Patent is hereby corrected as shown below:

Column 1,
Line 50, "a," should read -- a --.

Column 3,
Line 43, "DNAS" should read -- DNAs --;
Line 54, "preferablyused" should read -- preferably used -- and "tobe" should read -- to be --.

Column 6,
Line 32, "maybe" should read -- may be --.

Column 7,
Line 3, "DNA" should read -- $DNA_2$ --.

Column 9,
Lines 1-28 which read:

"MA-iL: 5'-GATCCGCGTTCTMCGACMTATGTAC-3'        (SEQ ID NO: 1)

S:       3'-GCGCMGATTGCTGTTATACATG-5'          (SEQ ID NO: 2)

MA2-2L: 5'-GATCTCTTAGCGTTCTMCGACAATATGTAC-3'   (SEQ ID NO: 3)

S:       3'-AGMTCGCMGATTGCTGTTATACATG-5'       (SEQ ID NO: 4)

MA-3L: 5'-GATCCACGATTAGCGTTCTMCGACAATATGTAC-3' (SEQ ID NO: 5)

S:       3'-GTGCTMTCGCMGATTGCTGTTATACATG-5'    (SEQ ID NO: 6)

UNITED STATES PATENT AND TRADEMARK OFFICE
CERTIFICATE OF CORRECTION

PATENT NO. : 6,248,534 B1
DATED : June 19, 2001
INVENTOR(S) : Kato et al.

It is certified that error appears in the above-identified patent and that said Letters Patent is hereby corrected as shown below:

<u>Column 9 cont'd.</u>

MA-4L: 5'-GATCGAGCACTCTTAGCGTTCTMCGACAATATGTAC-3'
(SEQ ID NO: 7)

S:  3-CTCGTGAGMTCGCAAGATTGCTGTTATACATG-5' (SEQ ID NO: 8)

MA-5L: 5'-GATCCTMCCTACCAGTTAGCGTTCTMCGACMTATGTAC-3'
(SEQ ID NO: 9)

S: 3'-GATTCGATGGTCMTCGCMGATTGCTGTTATACATG-5' (SEQ D NO: 10)

MA-6L:5'-GATCAGCGTTAGAGCCTTTAGTGCGTTCTMCGACAATATGTAC-3'
(SEQ D NO: 11)

S: (SEQ ID NO: 12)
3'-TCGCAATCTCGGMATCACGCMGATTGCTGTTATACATG-5'

FAM (5-carboxyfluorescein) labeled CIS adapter primer

5'-GTACATATTGTCGTTAGAACGC-3'  (SEQ ID NO: 13)"

should read:

--MA-iL: 5'-GATCCGCGTTCTAACGACAATATGTAC-3'  (SEQ ID NO: 1)

S:  3'-GCGCAAGATTGCTGTTATACATG-5'  (SEQ ID NO: 2)

MA2-2L: 5'-GATCTCTTAGCGTTCTAACGACAATATGTAC-3'  (SEQ ID NO: 3)

S:  3'-AG,AATCGCAAGATTGCTGTTATACATG-5'  (SEQ ID NO: 4)

MA-3L: 5'-GATCCACGATTAGCGTTCTAACGACAATATGTAC-3' (SEQ ID NO: 5)

S:  3'-GTGCTAATCGCAAGATTGCTGTTATACATG-5'  (SEQ ID NO: 6)

MA-4L: 5'-GATCGAGCACTCTTAGCGTTCTAACGACAATATGTAC-3'
(SEQ ID NO: 7)

UNITED STATES PATENT AND TRADEMARK OFFICE
CERTIFICATE OF CORRECTION

PATENT NO. : 6,248,534 B1
DATED : June 19, 2001
INVENTOR(S) : Kato et al.

It is certified that error appears in the above-identified patent and that said Letters Patent is hereby corrected as shown below:

<u>Column 9 cont'd.</u>

5: 3-CTCGTGAGAATCGCAAGATTGCTGTTATACATG-5' (SEQ ID NO: 8)

MA-5L: 5'-GATCCTAACCTACCAGTTAGCGTTCTAACGACAATATGTAC-3'
(SEQ ID NO: 9)

5: 3'-GATTCGATGGTCAATCGCAAGATTGCTGTTATACATG-5' (SEQ D NO: 10)

MA-6L:5'-GATCAGCGTTAGAGCCTTTAGTGCGTTCTAACGACAATATGTAC-3'
(SEQ D NO: 11)

5:3'-TCGCAATCTCGGAAATCACGCAAGATTGCTGTTATACATG-5'
(SEQ ID NO: 12)

FAM (5-carboxyfluorescein) labeled CIS adapter primer
5'-GTACATATTGTCGTTAGAACGC-3' (SEQ ID NO: 13)

<u>Column 13,</u>
Line 14, "themajority" should read -- the majority --.

<u>Column 18,</u>
Line 45, delete "and adapter-tagged stan-"; and
Line 46, delete "dard"

Signed and Sealed this

Tenth Day of September, 2002

Attest:

JAMES E. ROGAN
*Director of the United States Patent and Trademark Office*

*Attesting Officer*